US006203670B1

(12) United States Patent
Forat et al.

(10) Patent No.: US 6,203,670 B1
(45) Date of Patent: Mar. 20, 2001

(54) METHOD FOR GRAFTING A SUBSTITUTED DIFLUOROMETHYL GROUP

(75) Inventors: Gérard Forat, Lyons; Jean-Manuel Mas, Millery; Laurent Saint-Jalmes, Meyzieu, all of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/230,761

(22) Filed: Apr. 6, 1999

(30) Foreign Application Priority Data

Aug. 1, 1996 (FR) .................................. 96 09753
Aug. 1, 1996 (FR) .................................. 96 09754

(51) Int. Cl.[7] .............................. C07F 1/00; C07C 17/00
(52) U.S. Cl. .................. 204/157.6; 204/157.43; 204/157.79; 204/157.8; 204/157.94
(58) Field of Search .................. 204/157.78, 157.79, 204/157.8, 157.94, 157.43, 157.6

(56) References Cited

U.S. PATENT DOCUMENTS 5,859,288 * 1/1999 Forat et al. ........................ 562/113

FOREIGN PATENT DOCUMENTS

165135 * 12/1985 (EP) .
700885 * 3/1996 (EP) .
2593808 * 8/1987 (FR) .
2660923 * 10/1991 (FR) .

OTHER PUBLICATIONS

Stahly, "Trifluoromethylation of 1,3,5–Trinitrobenzene", J. of Flour. Chem., vol. 45, No. 3, pp. 431–433, Dec. 1989.*
Matsui et al., "A Convenient Trifluoromethylation of Aromatic Halides with Sodium Trifluoroacetate", Chem. Let., No. 12, pp. 1719–1720, Dec. 1981.*
Carr et al., "Sodium Perfluoroalkane Carboxylates as Sources of Perfluoroalkyl Groups", J. Chem. Soc., Perkin Trans. 1, No. 4, pp. 921–926, Apr. 1988.*

* cited by examiner

Primary Examiner—Edna Wong
(74) Attorney, Agent, or Firm—Burns, Doane, Swecker & Mathis, L.L.P.

(57) ABSTRACT

Provided is a process for grafting a substituted difluoromethyl group onto a compound bearing at least one electrophilic substituent, comprising (i) contacting the compound bearing at least one electrophilic substituent with a nucleophilic reagent which comprises (a) a fluorocarboxylic acid having the formula Ea—$CF_2$—COOH, wherein Ea is an electron-withdrawing atom or group, the fluorocarboxylic acid being at least partially salified with an organic or inorganic cation and (b) a polar aprotic solvent, and (ii) exposing the resulting medium of reaction to the action of microwave energy.

28 Claims, No Drawings

METHOD FOR GRAFTING A SUBSTITUTED DIFLUOROMETHYL GROUP

The present invention relates to a process for grafting a substituted difluoromethyl group onto a compound containing at least one electrophilic function, and which is useful in particular for preparing difluoro- or trifluoromethanesulphinic and -sulphonic acids and their salts.

The invention relates more particularly to a technique for perfluoroalkylating different compounds by nucleophilic substitution reactions or addition reactions typically carried out by organometallic derivatives.

Perfluoroalkylation techniques, or equivalent techniques, generally use derivatives of the perfluoroalkyl iodide type, in the presence of zinc. This technique is thus expensive, while at the same time requiring plants for processing the metal rejects, which need to be processed since zinc is a serious pollutant of water courses.

The other techniques, in which the perfluoroalkyl radial does not form an organometallic-type stabilized reactive intermediate, are generally difficult to carry out on account of the very poor stability of the free perfluoro anions in the reaction media. These anions generally lead to carbene-type products which, when they react, have lost one of their substituents.

In the specific case of perhaloalkanesulphonic acids and more particularly of trifluoromethanesulphonic acid, used as catalysts or as intermediates in organic synthesis, the process first known for preparing trifluoromethanesulphonic acid was electrochemical fluorination, as described in particular by R. D. Howels and J. D. McCown in Chemical Reviews, 1977, 77, 69.

At the present time, the process for preparing trifluoromethanesulphinic acid described in the European patent published under No. EP-165,136 is also known. This consists in placing a metal selected from zinc, aluminum, manganese, cadmium, magnesium, tin and iron, or even nickel and cobalt, in the presence of sulphur dioxide in a polar aprotic solvent and then in adding a trifluoromethyl halide at a pressure of more than $10^8$ Pa. This process gives a product in trifluoromethanesulphinate form in good yield. However, the sulphinate obtained is in a medium containing a large amount of zinc salt. The separation of the sulphinate and of the other salts of zinc poses a problem to be solved at the industrial level. Moreover, this technique, as well as the one described in the French patent application published under No. 2,593,808, required the use of perfluoroalkyl bromides which are reputed to be particularly harmful to the atmospheric layers, in particular on account of their strong greenhouse effect and their reputed harmful effect on ozone.

Accordingly, one of the aims of the present invention is to provide a reagent which allows a perfluoroalkylation according to a mechanism of the type involving a carbanion, without using organometallic reagents of transition metals such as zinc, and which uses products that are less harmful to the environment than, for example, trifluoromethyl bromide, while at the same time remaining low in cost.

It has often been sought to use perfluorocarboxylic acids as a source of perfluoroalkyl radials, ore generally of trifluoromethyl radicals, by carrying out decomposition reactions aimed at eliminating the carboxylic fragment from the said acids, thus releasing carbon dioxide. However, the successes which were obtained were very mixed and used particularly complicated catalytic systems. The perfluoroalkyl radicals or their equivalents generated by the decomposition of the said perfluorocarboxylic acids were moreover unstable in the reaction medium and required the use of stabilizers.

The present invention proposes to circumvent the drawbacks of the existing processes by providing a reagent which is not harmful to the environment and which is capable of giving the desired products in satisfactory yield.

In the course of the study which has led to the present invention, it has been demonstrated that a fluoroalkylation reaction is possible with a fluorocarboxylic acid salt, without a catalyst and without an agent capable of stabilizing the various intermediates envisaged obtained during the decomposition of the various perfluorocarboxylic acids, by working in a polar aprotic solvent and under the action of microwaves.

The abovementioned aims and others, which will become apparent hereinbelow, are thus achieved according to the invention by a process for grafting a substituted difluoromethyl group onto a compound containing at least one electrophilic function, which comprises the steps consisting in:

i) placing the said compound containing at least one electrophilic function in the presence of a nucleophilic reagent comprising:
a) a fluorocarboxylic acid of formula Ea—$CF_2$—COOH in which Ea represents an electron-withdrawing atom or group, which is at least partially salified with an organic or inorganic cation, and
b) a polar aprotic solvent; and then
ii) exposing the reaction medium to the action of microwaves.

The electrophilic functions capable of reacting with the reagent of the present invention are the functions which usually react with organometallic reagents, and will be described in detail hereinbelow.

The first essential feature of the invention relates to the reagent.

As has been mentioned above, the solvent plays an important role in the present invention and must be aprotic, and advantageously polar and preferably contains very few impurities bearing an acidic hydrogen, as will be seen hereinbelow.

It is thus preferable for the polar aprotic solvent which can be used to have a significant dipolar moment. Thus, its relative dielectric constant e is advantageously at least equal to about 5 (the positional zeros are not considered as significant figures in the present description unless otherwise specified). Preferably, e is less than or equal to 50 and greater than or equal to 5.

It is also preferred for the solvents of the invention to be capable of solvating the cations well, which can be codified by the donor index D of these solvents. It is thus preferable for the donor index D of these solvents to be between 10 and 30. The said donor index corresponds to the DH (heat difference), expressed in kilocalories, for the combination of the said polar aprotic solvent with antimony pentachloride.

According to the present invention, it is preferable for the reagent not to have any acidic hydrogens on the polar solvent(s) it uses. In particular, when the polar nature of the solvent(s) is obtained by the presence of electron-withdrawing groups, it is desirable for there to be no hydrogen alpha to the electron-withdrawing function.

More generally, it is preferable for the pKa corresponding to the first acidity of the solvent to be at least equal to about 20 ("about" emphasizing that only the first figure is significant), advantageously at least equal to about 25, preferably between 25 and 35.

It is preferable for the said fluorocarboxylic acid or acid salt to be at least partially, preferably completely, soluble in the medium constituting the reagent.

Solvent which give good results can be, in particular, amide-type solvents. Among the amides which are also included are amides with a specific nature, for instance tetrasubstituted ureas and monosubstituted lactams. The amides are preferably substituted (disubstituted in the case of the ordinary amides). Mention may be made, for example, of pyrrolidone derivatives, such as N-methylpyrrolidone, or alternatively N,N-dimethylformamide or N,N-dimethylacetamide.

Another particularly advantageous category of solvents consists of the ethers, which may be either symmetrical or unsymmetrical and may be either open or closed. The category of ethers should include the various derivatives of glycol ethers, such as the various glymes, for example diglyme.

It was also found that the decomposition of fluorocarboxylic acids can be obtained in a particularly effective manner when the content of labile hydrogens in the system, or more exactly of releasable protons, is less than the content of fluoro groups released by the decomposition of the fluorocarboxylic acid salts. The terms "labile hydrogen" and "releasable proton" mean a hydrogen atom which can be stripped out in the form of a proton by a strong base. In practice, these are the protons of acidic functions which have a pKa of less than about 20 (the word "about" emphasizes the fact that the number 20 has only one significant figure).

Preferably, the content of releasable protons borne by the various components of the reagent, including their impurities, is not more than half of the initial molar concentration of the said fluorocarboxylic acid.

The lower the content of releasable protons in the reagent, the lower the risk of a side reaction will be and the better the yield will be.

Thus, it is preferable for, in the reagent, the content of labile hydrogen atoms to be not more than 10%, preferably not more than 1% (on a molar basis) relative to the initial content of the said fluorocarboxylic acid.

The main impurity bearing labile hydrogen atoms is generally water, which is capable of releasing up to two hydrogen atoms per molecule.

In general, it is preferable to use reagents and solvents which have been dried thoroughly, such that the weight content of water in the reaction medium is not more than 1 per 1000, advantageously not more than 5 per 10,000, preferably not more than 1 per 10,000. However, in the course of the study which has led to the present invention, it has been shown that, in order to maximize the yields, it is prudent to work such that the water content does not fall to zero. In particular, it is preferred for the water content to be at least equal to about 10 ppm (by mass), advantageously to about 50 ppm, preferably to about 100 ppm. Relative to the fluorocarboxylic acid concentration, it is preferable for the molar content of water to be not more than about 5000 ppm, advantageously not more than about 1 per 1000, preferably not more than about 5 per 10,000. It is also prudent to work such that the water content does not fall to zero; in particular, it is preferred for the water content (on a molar basis) to be at least equal to about 50 ppm, advantageously to about 200 ppm, relative to the fluorocarboxylic acid concentration.

Moreover, it has been possible to show that other elements, namely transition elements, especially those with two stable valency states, such as copper or europium, could be not without harm, or could even be harmful (this is the case in particular for copper and lanthanides with stable valencies) for the invention.

Although this reagent according to the invention does not require a catalyst, such metal elements can be present as impurities introduced in particular by the solvent.

Thus, it is preferable for the molar content of these elements to be less than 1000 ppm, advantageously less than 100 ppm, preferably less than 10 ppm relative to the initial content of the said fluorocarboxylic acid.

Furthermore, although it has been recommended many times to use elements from column VIII of the Periodic Table of the Elements with perfluoroacetic acid, in order to promote certain substrates and to promote certain types of reaction, this proved to be particularly harmful for the reaction targeted above. Accordingly, it is preferable to use reagents not containing any metals from column VIII, in particular platinium mine metals, which is the group consisting of platinum, osmium, iridium, palladium, rhodium and ruthenium.

In the present description, reference is made to the supplement to the bulletin of the French Chemical Society No. 1, January 1966, in which a periodic table of the elements was published.

Thus, it is preferable for the content of platinum mine metals, or even of metals from column VIII, to be less than 100 ppm, advantageously less than 10 ppm, preferably less than 1 ppm. These values are given relative to the starting fluorocarboxylic acid and are expressed on a molar basis.

In a more general and more empirical manner, it can be pointed out that these two categories of metals, namely transition elements and especially those with two stable valency states, and the elements from column VIII, must be present in the reagent at an overall concentration level of not more than 1000 molar ppm, preferably not more than 10 molar ppm.

It will be noted that the various metals present at such an overall concentration level are in extremely low amount and, in this respect, they play no catalytic role. Their presence does not improve the reaction kinetics, or is even harmful thereto when they are present in excessive amount.

The use, in addition to the components of the abovementioned reagents, of alkali metal fluoride or of quaternary ammonium fluoride, which are usually present in reagent systems using fluorocarboxylates, did not prove to be harmful, but proved to be of little value, in particular on account of the fact that it produces saline effluents which are difficult to process. Accordingly, it is preferable to limit their content, in particular their initial content. Thus, it is preferable for the content of fluoride, which is termed as ionic, i.e. capable of being ionized in the polarizing medium for the reagent, is not more than the initial molar concentration of the said fluorocarboxylic acid salt, advantageously a half and preferably a quarter of this concentration.

In the fluorocarboxylic acid of the constituent a) of the reagent of the invention, the species Ea which exerts an electron-withdrawing effect on the difluoro carbon atom is preferably selected from the functional groups whose Hammett constant $s_p$ is at least equal to 0.1. It is also preferable for the inductive component of $s_p$, $s_L$, to be at least equal to 0.2, advantageously to 0.3. In this respect, reference will be made to the book by March, "Advanced Organic Chemistry", third edition, John Wiley and Son, pages 242 to 250, and in particular Table 4 of this section.

More particularly, the electron-withdrawing species can be selected from halogen atoms, preferably light halogens, in particular chlorine and fluorine. The corresponding fluorocarboxylic acid is a halofluoroacetic acid of formula (1) X—$CF_2$—COOH in which X is a halogen atom, advantageously a light halogen (chlorine or fluorine).

Ea can also be selected advantageously from nitrile, carbonyl, sulphonic and perfluoroalkyl groups. Fluorocarboxylic acids of this type which can be used correspond to formula (2) R—G—CF$_2$—COOH in which R—G represents a nitrile group or G represents >C—O or >S=O, or —(CF$_2$)$_n$— in which n is greater than or equal to 1, and R represents any organic or inorganic residue, preferably an organic radical such as aryl, alkyl or arylalkyl, which is optionally substituted. R can also represent an inorganic or organic solid support, such as a resin.

When G represents a perfluoroalkylene group —(CF$_2$)$_n$—, n is advantageously between 1 and 10, preferably between 1 and 5. Again in this case, R can also represent a halogen atom, in particular fluorine.

Generally, except when the fluorocarboxylic acid is a polymer, the total number of carbon atoms in the fluorocarboxylic acid advantageously does not exceed 50.

The counter-cations capable of forming a salt with the said fluorocarboxylic acid are advantageously bulky. Thus, alkali metal salts are preferred, advantageously those in which the alkali metal is selected from sodium, potassium, rubidium, caesium and francium. Preferably, the said metal is from a period which is at least equal in rank to that of sodium, advantageously to that of potassium. Quaternary ammonium salts are also preferred. For the same period, alkaline-earth metals give results similar to those of the alkali metals.

It is also possible to improve the reaction by using carions which are either naturally bulky, for instance quaternary ammonium or quaternary phosphoium cations, or which are made bulky by the addition of chelating agents or preferably cryptands, such as, for example, crown ethers or derivatives which are both aminated and oxygenated.

Perfluorocarboxylic acid salts can advantageously be used, such as trifluoroacetate, perfluoropropionate and perfluorobutyrate of an alkali metal, in particular of potassium.

The reagent reacts, according to the invention, with an electrophilic compound containing an electrophilic atom, it being possible for this atom to be a carbon atom or a hetero atom, for example sulphur, selenium or tellurium. It advantageously reacts with hydrocarbon-based compounds on an electrophilic carbon atom not belonging to an aromatic system.

According to a first aspect of the invention, the reagent preferably reacts with compounds containing an electrophilic atom, advantageously an electrophilic hetero atom, linked to an atom, in particular a halogen atom, or to a pseudo-halogen group which can be substituted in a single step.

The reaction works all the better when, in contrast with an SN2 reaction, it proceeds via a reaction intermediate originating from an addition onto a multiple bond or onto a doublet.

When the electrophilic atom is a sulphur atom, mention may be made of the reaction with:

halo or pseudo-halo derivatives of organosulphur compounds, in particular sulphenyl, sulphinyl or sulphonyl halides, in which the halogen atom or the pseudo-halogen group is substituted, during the reaction, with a substituted difluoromethyl group;

disulphides, for example optionally substituted aryl disulphides, in which the S S bond is broken and replaced with a substituted difluoromethyl group; suitable disulphides may be, in particular, C$_5$–C$_{10}$ aryl disulphides, optionally substituted with a C$_1$–C$_{10}$ alkyl, C$_1$14 C$_{10}$ alkoxy or nitro group or with one or more (E3) halogen atoms;

sulphur oxides, such as sulphur dioxide;

thiocyanate-type compounds in which the cyano group is substituted during the reaction with a substituted difluoromethyl group; preferred thiocyanates are C$_5$–C$_{10}$ aryl thiocyanates, including alkylaryl thiocyanates, and C$_1$–C$_{10}$ alkyl thiocyanates, including arylalkyl thiocyanates.

In the above compounds, the halogen atom can be selected from iodine, bromine, chlorine and fluorine atoms. A "pseudo-halogen" group is a group which, when leaving, in an ionic form, has an associated acid whose pKa is less than 4, preferably less than 3, in particular less than 0.

The preferred groups are those whose associated acid has an acidity (measured by the Hammett constant) at least equal to that of acetic acid, advantageously to that of sulphonic acids, or trihalo acids. One of the typical pseudo-halogens is a perfluoroalkanesulphonyloxy group which releases a perfluoroalkanesulphonate. Preferred pseudo-halogen groups can be selected from tosylate (p-toluenesulphonyloxy), mesylate (methylsulphonyloxy), trifluoromethylsulphonyloxy and trifluoroacetoxy groups. The acetate group can also be considered as such a leaving group.

Among these groups, the perfluoroalkanoyloxy groups such as trifluoroacetyloxy are very advantageous when it is desired to graft a perfluoroalkyl group (trifluoromethyl when the initial group is the trifluoroacetyloxy group). For example, substitution of the trifluoroacetyloxy group regenerates the reagent in situ, releasing into the medium trifluoroacetic acid or one of its salts, which can in turn react as a source of trifluoromethyl groups.

According to another aspect, the reagent also reacts advantageously with a compound selected from carbonyl compounds such as ketone, aldehyde, acid halide or activated ester, carrying out an addition on the carbonyl function.

Mentioned may be made, as preferred and non-limiting examples, of aromatic aldehydes, which are preferably C$_5$–C$_{10}$, in which the aromatic ring can optionally be substituted with a C$_1$–C$_{10}$ alkyl, C$_1$–C$_{10}$ alkoxy or nitro group or with a halogen atom; cyclic ketones such as cyclohexanone; non-enolizable ketones activated by a donor group, such as trifluoromethylacetophenone; aromatic anhydrides, such as benzoic anhydride.

In this case, the reaction product is generally an alcohol (for example in alkoxide form) in which the carbon atom bearing the hydroxyl function is substituted with a substituted difluoromethyl group. This product can then optionally react with the reagent or with the starting material depending on the reaction conditions.

In general, the amount of reagent used in the process of the invention will be determined in a manner which is known per se, depending on the functionality of the electrophilic compound.

It is generally preferable for the ratio to be between 1 and 10, and advantageously about 2, electrophilic functions per fluorocarboxylic acid molecule.

It should be pointed out that the product obtained from the decomposition of the fluorocarboxylic acid can react with itself if it contains one of the functions capable of reacting.

It may be noted that compounds containing an electrophilic function which are in liquid form can be used as solvent according to the present invention provided that they are aprotic. The reaction of the present invention can thus advantageously be carried out by placing a) a fluorocarboxylic acid salt as defined above, in contact with b) a compound containing at least one electrophilic function acting both as solvent and as reaction substrate.

During the use of the reagent according to the invention with a substrate containing at least one electrophilic function, it is important for this substrate to cause the least possible disruption to the conditions described above.

Thus, it is preferable to use a sufficiently dried substrate, or one which contains no acidic hydrogens which can be stripped out with strong bases or any harmful impurities, i.e., in general, a substrate which satisfies the same constraints as those outlined for the reagent.

One of the aspects of the present invention relates more particularly to the application of the process claimed to the preparation of organic oxysulphide and fluoro derivatives from a sulphur oxide, in particular sulphur dioxide. This in particular allows fluorosulphinic or fluorosulphonic acids to be formed.

In the course of the study which has led to the present invention, it has thus been demonstrated that it is possible to graft onto a sulphur oxide fluoroalkyl radicals generated from a fluorocarboxylic acid, without a catalyst and without an agent capable of stabilizing the various intermediates envisaged obtained during the decomposition of the various perfluorocarboxylic acids, in satisfactory conversion yield and selectively and with remarkably high kinetics, by working in a polar aprotic solvent and under the action of microwaves.

In this specific case, it is preferable for the ratio of the relative amounts of the said initial fluorocarboxylic acid and of sulphur oxide, preferably dioxide, to be between 1 and 10, and advantageously about 2, sulphur atoms per fluorocarboxylic acid molecule.

When the said oxide is sulphur dioxide, the mixture resulting from step a) can comprise two phases in equilibrium and can thus contain a liquid phase, in which at least some of the said acid and of the sulphur dioxide are dissolved in the said solvent, in equilibrium with a gaseous phase which contains sulphur dioxide.

Still in the case of sulphur dioxide, the product obtained by heating the reagent is a sulphinic acid or a sulphinic acid salt whose counterion is that of the starting fluorocarboxylic acid salt.

In order to go from the sulphinic acid to the corresponding sulphonic acid, the reaction product or the purified reaction product should be subjected to an oxidation, which is known per se, in particular using aqueous hydrogen peroxide solution or sodium hypochlorite. A process for purifying sodium trifluoromethylsulphinate, and for oxidizing to sulphonate, which can be applied according to the invention, is described in the European patent application published under No. EP-A-0,396,458. The sulphinic or sulphonic acid salts thus obtained can be converted into the corresponding free acids in an acidic medium. The reaction products, salts or free acids, can be readily isolated and used in the subsequent organic synthesis steps. Thus, for example, starting with fluorosulphinic acids, the corresponding sulphinyl chlorides can be prepared. The second essential element of the invention consists in reacting the reagent with the electrophilic compound under the action of the microwaves.

Exposure of the reaction medium to the action of microwaves allows the medium to be activated, in a comparable manner to the temperature within this medium. It is found that this activation affords a noteworthy enhancement of the reaction kinetics. Depending on the power applied, the reaction time can range in particular from 30 seconds to 1 hour, in particular from 1 to 30 minutes.

It is difficult to define the temperature of a medium during the exposure to microwaves. However, it is possible to indicate that the temperature of the medium before the action of the microwaves is advantageously between the commencing freezing point of the medium and 110° C.

The medium subjected to microwaves can also be circulated in a cooling device so as to keep the temperature of the reaction medium leaving the region of exposure to microwaves at not more than 150° C., advantageously not more than 130° C., preferably not more than 120° C.

The exposure of the reaction medium to microwaves is advantageously such that the medium is subjected to radiation with an energy at least equal to 1 wall per second and per kg of reaction mass, preferably at least equal to 5 W/s/kg.

When the inlet product is fragile, it is recommended for the radiated energy to be not more than about 100 W/s/kg, advantageously not more than about 50 W/s/kg, preferably not more than about 20 W/s/kg.

The frequency of the microwaves which can be used is between about 100 MHz and about 10 GHz, advantageously between about 300 MHz and 3 GHz. The wavelength of the microwaves which can be used is generally between 10 cm and 1 m in air.

The microwaves will advantageously be applied for a duration and at an intensity corresponding to at least 5 walls per second and per mole of fluorocarboxylic acid, preferably at least about 20 W/s/mol.

When the inlet product is fragile, it is recommended for the radiated energy to be not more than 1000 W/s/mol of fluorocarboxylic acid, advantageously not more than about 500 W/s/mol of fluorocarboxylic acid, preferably not more than about 200 W/s/mol of fluorocarboxylic acid.

In the specific case in which the process claimed is applied to the preparation of organic oxysulphide and fluoro derivatives as described above, the microwaves will advantageously be applied for a duration and at an intensity corresponding to at least 5 watts per second and per mole of fluorocarboxylic acid, preferably at least about 20 W/s/mol.

The microwaves can be applied to the reaction medium by any means which is known per se.

Advantageously, the microwave applicator is in the form of a cavity (reactor) containing the reaction medium. Internal elements which dissipate strongly under microwave radiation and which transmit the energy to the reaction medium can also be placed inside the reactor.

The geometry of the device will advantageously be defined as a function of the characteristics of energy dissipation by the reaction medium.

Preferably, only one wave mode will be excited, in order to allow the best possible control over the energy dissipation. In this case, reactors designed for continuous processes, whose simple geometry (usually cylindrical) is suited to the monomodal transmission of the waves, will be preferred. These continuous reactors can function with recycling of the reaction medium.

The applicator can in particular be in the form of a tubular reactor arranged parallel to a waveguide with radiating slits.

Nevertheless, "hatch"-type reactors for discontinuous processes can also be used in order to expose the reaction medium to the microwaves in monomodal form. The thermal homogeneity of the reaction medium is advantageously ensured by rotating the reactor and/or by counter-sense stirring of the medium with a glass paddle stirrer.

The exposure to microwaves may optionally be coupled with a conventional mode of heating.

The examples which follow illustrate the invention.

EXAMPLE 1

Preparation of Phenyl Trifluoromethyl Sulphide 2.26 g (14.9 mmol) of anhydrous potassium trifluoroacetate, 1.6 g (7.4 mmol) of phenyl sulphide and 17 g of anhydrous dimethylformamide (DMF) are loaded into a 30 ml Teflon reactor.

The molar ratio of the potassium trifluoroacetate to the phenyl disulphide is 2.0.

The water content of the reaction medium is less than 0.002 mol % relative to the trifluoroacetate.

The reactor is closed and then placed in a microwave oven of maximum power 300 W with a monomodal system at a frequency of 2450 MHz, the microwaves being focused at the base of the reactor using a waveguide.

Microwave emission is then carried out for 10 minutes at a rate or 2.5 W/s/kg of reaction mass (cumulative power: about 30 W) and then for 5 minutes at a rate of 10 W/s/kg (cumulative power in this second step: about 60 W).

After cooling, the reaction mass is analysed by gas chromatography and $^{13}F$ NMR.

It is determined that the degree of conversion of the disulphide (amount of disulphide disappeared/amount of initial disulphide) is 69%.

The actual yield of phenyl trifluoromethyl sulphide (amount of phenyl trifluoromethyl sulphide formed relative to the amount of initial phenyl disulphide) is 55.4%, which corresponds to a selectively, expressed by the conversion yield for the disulphide (amount of phenyl trifluoromethyl sulphide formed relative to the amount of phenyl disulphide converted), of 80.4%.

In the same way, it is determined that the degree of conversion of the potassium trifluoroacetate is 62% and that the selectivity for the conversion into phenyl difluoromethyl sulphide is 87.5%.

Comparative Example 1

The same reaction is carried out without using microwaves.

The reagents are loaded into a 30 ml glass tube with magnetic stirring, as in Example 1, and are then heated at 140° C. for 20 hours.

After cooling, the mixture is assayed by gas chromatography to determine the following results:

degree of conversion of the phenyl disulphide: 67% yield for conversion of phenyl disulphide into phenyl trifluoromethyl sulphide (selectivity): 76%.

It is found that a degree of conversion is achieved which is similar, in a few minutes under microwaves, to that obtained in more than one day with conventional heating, with a gain in selectivity of close to 5%. The process of the invention thus gives better performance than a traditional heating process.

EXAMPLE 2

Preparation of Trifluoromethylsulphinic Acid 13 g of N-methylpyrrolidone (NMP; water content of less than 10 ppm by weight), 1.6 g of $CF_3CO_1K$ (water content of less than 100 ppm by weight) and about 2 g of gaseous sulphur dioxide (water content of less than 0.01 mol %), by bubbling into the liquid, are introduced into a 30 ml Teflon tubular reacter on which is mounted a manomer ranging from 0 to 20 bar, and a degassing valve.

The $CF_2CO_2K/SO_2$ molar ratio is about 2. The $CF_3CO_2K/SO_2$ mass ratio is about 0.13.

This closed reactor is introduced into a microwave of maximum power 300 W with a monomodal system at a frequency of 2450 MHz, the microwaves being focused at the base of the reactor using a waveguide.

Emission of microwaves is then carried out for 10 minutes at a rate of 10 W/s/kg of reaction mass, i.e. a total power of about 30 W. The pressure rises from 0 to 2 bar ($2 \times 10^5$ Pa) during the reaction, to return to zero after stopping the microwaves and cooling the reaction medium.

The reaction mixture is then taken up in water and analysed by $^{13}F$ NMR and HPIC (high performance ionic chromatography) in separation mode.

The degree of conversion, the actual yield of $CF_3SO_2K$ and the conversion yield are determined, and are given in Table 1 below for Examples 1 to 6.

EXAMPLE 3

Example 2 is repeated, while maintaining a $CF_3CO_2K/SO_2$ ratio of between 1.9 and 2.1 and by applying the microwaves for 7 minutes at a rate of 10 W/s/kg for a total power of 45 W. The pressure in the reactor passes through a maximum of $3.8 \times 10^6$ Pa during the reaction.

EXAMPLE 4

Example 2 is repeated, while maintaining a $CF_3SO \cdot K/SO$ ratio of between 1.9 and 2.1 and by applying the microwaves for 4 minutes at a rate of 10 W/s/kg for a total power of 60 W. The pressure in the reactor passes through a maximum of $3 \times 10^5$ Pa during the reaction.

Comparative Example 2

Preparation of Trifluoromethylsulphinic Acid Without Using Microwaves 42 g of N-methylpyrrolidone (NMP), then 5.32 g (35 mmol) of potassium trifluoroacetate and lastly 4.9 g (76 mmol) of gaseous sulphur dioxide, by bubbling into the liquid, are introduced into a 100 ml Hastalloy reactor stirred by a turbomixer. The sulphur dioxide is completely dissolved by the NMP.

The molar ratio of the sulphur dioxide to the potassium trifluoroacetate is 1.5.

The water content of the reaction mixture is 0.1% by weight relative to the weight of the mixture, i.e. a molar ratio of the water to the trifluoroacetate of 0.07.

The mixture is heated in the closed reactor at a temperature of 140° C. for 6 hours with stirring.

During the reaction, the pressure inside the reactor, returned to an ambient temperature, is $3.5 \times 10^5$ Pa relative to the initial pressure.

The reaction medium is then taken up in water and analysed by $^{19}F$ NMR in order to assay the conversion of the potassium trifluoroacetate.

The degree of conversion (DC) of the starting potassium trifluoroacetate, expressed by the molar table of the amount of trifluoroacetate consumed (converted) to the initial amount, is 61.7%.

The actual yield (AY) expressed by the molar ratio of the amount of trifluoromethyl sulphinate formed, in free or salified form, to the amount of initial trifluoroacetate, is 29.7%.

The yield relative to the product converted (CY), expressed by the molar ratio of the amount of trifluoromethyl sulphinate formed, in free or salified form, to the amount of trifluoroacetate converted, is 48.1%. The product is isolated in the form of the potassium salt.

EXAMPLES 5–7

These examples illustrate the effect of microwaves when the reaction of Example 2 is carried out in dimethylformamide (DMF).

The general operating conditions are identical except that the NMP is replaced with DMF.

Three different conditions are applied for the microwaves:

Example 5: 7 minutes for a total power of 45 W;

Example 6: 7 minutes for a total power of 45 W with addition of one molar equivalent of KF relative to $SO_2$;

Example 7: 5 minutes for a total power of 60 W.

The results are summarized in Table 1 below.

TABLE 1

| Example | Composition of the reagent | Reaction time | Microwave power (W) | DC (%) | AY (%) | CY (%) |
|---|---|---|---|---|---|---|
| 2 | NMP $H_2O$: 0.002% by weight | 10 min | * 30 | 26.4 | 12.2 | 46.2 |
| 3 | NMP $H_2O$: 0.002% by weight | 7 min | * 45 | 69.6 | 34.5 | 19.6 |
| 4 | NMP $H_2O$: 0.002% by weight | 4 min | * 60 | 52 | 25 | 48 |
| Comp 2 | NMP $H_2O$: 0.1% by weight | 6 h | — | 61.7 | 29.7 | 48.1 |
| Comp 3 | NMP $H_2O$: 4% | 7 min | * 45 | 77 | 20.3 | 26.4 |
| 5 | DMF $H_2O$: 0.002% by weight | 7 min | * 45 | 30.4 | 17.6 | 57.9 |
| 6 | DMF $H_2O$: 0.002% by weight | 7 min | * 45 | 70.9 | 31.8 | 44.9 |
| 7 | DMF $H_2O$: 0.002% by weight | 5 min | * 60 | 44.6 | 24.3 | 54.8 |
| Comp 4 | DMF $H_2O$: 0.002% by weight | 6 h | — | 80.4 | 33.8 | 41.7 |
| Comp 5 | DMF $H_2O$: 2% by weight | 5 min | * 60 | 32.4 | 16.2 | 50 |

In all of the examples according to the invention, it is found that results similar to those obtained in six hours by simple heating (Comparative Example 4) are achieved in a few minutes with microwaves.

Comparative Examples 3 and 5 show that the presence of water in large amounts in the reaction medium is harmful to the production of potassium trifluoromethylsulphinate in satisfactory amount.

The conditions described in Examples 2 to 7 are adapted to the preparation of other oxysulphide compounds such as, in particular, pentafluoroethylsulphinic acid (from $C_2F_5COOK$) or heptafluoropropylsulphinic acid (from $C_3F_7COOK$) in potassium sulphinate form.

EXAMPLE 8

Preparation of Trifluoromethylsulphinyl Chloride

Potassium trifluoroacetate is prepared under the conditions of Example 7.

The DMF is removed from the reaction mixture by distillation under vacuum at a temperature not exceeding 55–60° C.

The distillation residue is taken up in acetonitrile and then filtered. The filtrate is distilled in order to remove the solvent and the potassium trifluoroacetate is isolated in a purification yield of 96% relative to the crude reaction mixture, assayed by ionic chromatography.

The product resulting from this operation is taken up in toluene and thionyl chloride $SO_2Cl_3$ is added in stoichiometric amount relative to the trifluoromethylsulphinate. The trifluoromethylsulphinyl chloride is obtained in a yield of 65%.

What is claimed is:

1. A process for grafting a substituted difluoromethyl group onto a compound bearing at least one electrophilic substituent, comprising (i) contacting said compound bearing at least one electrophilic substituent with a nucleophilic reagent which comprises (a) a fluorocarboxylic acid having the formula Ea—$CF_2$—COOH, wherein Ea is an electron-withdrawing atom or group, said fluorocarboxylic acid being at least partially salified with an organic or inorganic cation and (b) a polar aprotic solvent, thereby forming a medium of reaction, and (ii) exposing the resulting medium of reaction to the action of microwave energy.

2. Process according to claim 1, wherein the polar aprotic solvent is the compound containing at least one electrophilic function.

3. Process according to claim 1, wherein a content of releasable protons borne by the various components of the reagent, including their impurities, is not more than half of the initial molar concentration of the fluorocarboxylic acid.

4. Process according to claim 3, wherein the proton content is not more than 10% of the initial molar concentration of the fluorocarboxylic acid salt.

5. Process according to claim 1, wherein a weight content of water in the reaction medium is not more than 1 per 1000.

6. Process according to claim 1, wherein a water content of the reaction medium is not more than 10 ppm by weight.

7. Process according to claim 1, wherein the molar ratio of a water content of the reaction medium to the concentration of fluorocarboxylic acid is not more than 5000 ppm.

8. Process according to claim 1, wherein the molar ratio or a water content of the reaction medium to the concentration of fluorocarboxylic acid is at least equal to 50 ppm.

9. Process according to claim 1, wherein a content of transition elements in the reagent is less than 1000 molar ppm relative to the at least partially salified fluorocarboxylic acid.

10. Process according to claim 1, wherein a content of elements from column VIII of the Periodic Table of the Elements in the reagent is less than 100 molar ppm relative to the fluorocarboxylic acid.

11. Process according to claim 1, wherein a content, expressed in equivalents, of ionic fluoride in the reagent is not more than the initial molar concentration of the fluorocarboxylic acid.

12. Process according to claim 1, wherein the donor index of the polar aprotic solvent is between 10 and 30.

13. Process according to claim 1, wherein the pKa corresponding to the first acidity of the solvent is at least equal to 20.

14. Process according to claim 1, wherein the electron-withdrawing atom or group is selected from electron-withdrawing groups whose Hammet constant $s_p$ is at least equal to 1.

15. Process according to claim 1, wherein the acid is selected from the group consisting of compounds of formula (1) X—CF$_2$—COOH, in which X represents a halogen atom, and the compounds of formula (2) R—G—CF$_2$—COOH, in which R—G represents a nitrile group or G represents >C=0 or >S=0, or —(CF$_2$)$_n$—where n is greater than or equal to 1, and R represents any organic or inorganic residue.

16. Process according to claim 1, wherein the fluorocarboxylic acid or the at least partially salified fluorocarboxylic acid salt is completely soluble in the reaction medium.

17. Process according to claim 1, wherein the at least partially salified fluorocarboxylic is a salt of an alkali metal selected from the group consisting of sodium, potassium, rubidium, cesium and francium, or a quaternary ammonium salt.

18. Process according to claim 1, wherein the solvent is selected from N-disubstituted amides or cyclic or non-cyclic ethers.

19. Process according to claim 1, wherein the compound bearing at least one electrophilic substituent is selected from halo or pseudo-halo derivatives of organosulphur compounds; sulphur oxides; thiocyanates; disulphides; or compounds of ketones, aldehydes, acid halides or activated esters.

20. Process according to claim 1, wherein the compound bearing at least one electrophilic substituent does not contain any hydrogens which can be stripped out with a strong base.

21. Process according to claim 1, wherein the microwave power applied is at least 1 watt per second and per kg of reaction mass.

22. Process according to claim 1, wherein the microwave power applied is at least 5 watts per second and per mole of fluorocarboxylic acid.

23. Process according to claim 1, wherein the microwave power applied is not more than 100 watts per second and per kg of reaction mass.

24. Process according to claim 1, wherein the reaction medium is exposed to the microwave energy in a region, and the reaction medium leaves the region at a temperature of not more than 150° C.

25. Process according to claim 1, wherein the compound bearing at least one electrophilic substituent is sulphur dioxide.

26. Process according to claim 25, wherein a sulphinic acid salt is obtained in step (i), and further comprising in step (i), oxidizing the sulphinic acid salt obtained in step (i) by placing the product of step (i) in contact with an oxidation reagent.

27. Process according to claim 1, wherein the medium of reaction in step (i) is a liquid in equilibrium with a gaseous phase containing sulphur dioxide.

28. Process according to claim 1, wherein the compound bearing at least one electrophilic substituent is a sulphur oxide, and an organic oxysulphide or fluoro derivative is prepared by step (ii).

* * * * *

UNITED STATES PATENT AND TRADEMARK OFFICE
CERTIFICATE OF CORRECTION

PATENT NO. : 6,203,670 B1
DATED : March 20, 2001
INVENTOR(S) : Gérard Forat et al.

It is certified that error appears in the above-identified patent and that said Letters Patent is hereby corrected as shown below:

Title page,
After "Item [21], Appln. No.: 09/230,761", please insert

-- PCT Filed: July 30, 1997
PCT No.: PCT/FR97/01423
§ 371 Date: April 6, 1999
§ 102(e) Date: April 6, 1999
PCT Pub No.: WO98/05609
PCT Pub. Date: Feb. 12, 1998 --

Signed and Sealed this

Eleventh Day of December, 2001

Attest:

NICHOLAS P. GODICI
Attesting Officer   Acting Director of the United States Patent and Trademark Office